US009136051B2

(12) United States Patent
Park et al.

(10) Patent No.: US 9,136,051 B2
(45) Date of Patent: *Sep. 15, 2015

(54) MICROROBOT SYSTEM FOR INTRAVASCULAR THERAPY AND METHOD OF CONTROLLING THE SAME

(75) Inventors: Suk Ho Park, Gwangju (KR); Jong Oh Park, Gyeonggi-do (KR); Hyun Chul Choi, Jeollanam-do (KR); Kyoung Rae Cha, Gwangju (KR); Se Mi Jeong, Jeollabuk-do (KR)

(73) Assignee: Industry Foundation of Chonnam National University, Gwangju (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/697,110

(22) PCT Filed: Jun. 4, 2012

(86) PCT No.: PCT/KR2012/004381
§ 371 (c)(1),
(2), (4) Date: Nov. 9, 2012

(87) PCT Pub. No.: WO2013/032113
PCT Pub. Date: Mar. 7, 2013

(65) Prior Publication Data
US 2013/0072789 A1  Mar. 21, 2013

(30) Foreign Application Priority Data
Aug. 31, 2011 (KR) ......................... 10-2011-0087546

(51) Int. Cl.
*A61B 1/04* (2006.01)
*H01F 7/02* (2006.01)
(52) U.S. Cl. (Continued)
CPC .. *H01F 7/02* (2013.01); *A61B 6/12* (2013.01); *A61B 19/2203* (2013.01);
(Continued)

(58) Field of Classification Search
CPC ............... A61B 19/52; A61B 19/5244; A61B 1/00156; A61B 2019/5251; A61B 2019/5276; A61B 6/12; A61B 19/2203; A61B 2019/2219; A61B 2019/2249; A61B 2019/2253; H01F 7/02; A61N 2/002

USPC .................................................. 600/407–430
See application file for complete search history.

(56) References Cited

U.S. PATENT DOCUMENTS 4,757,290 A * 7/1988 Keren ........................... 333/219
6,515,657 B1 * 2/2003 Zanelli .......................... 345/419
(Continued)

FOREIGN PATENT DOCUMENTS

KR 10-2005-0121059 A 12/2005
KR 10-2010-0104504 A 9/2010
(Continued)

OTHER PUBLICATIONS

EMA system with gradient and uniform saddle coils for 3D locomotion of microrobot by Choi et al. Aug. 2010.*

Primary Examiner — Sanjay Cattungal
(74) Attorney, Agent, or Firm — Rabin & Berdo P.C.

(57) ABSTRACT

The present invention relates, in general, to a microrobot system for intravascular therapy and, more particularly, to a microrobot system for intravascular therapy, which removes thrombus, clots and occlusions that are clogging blood vessels using the fast rotary power of a spherical microrobot having protrusions, thus treating clogged blood vessels.

The microrobot system for intravascular therapy according to the present invention includes a spherical microrobot unit (100') including a magnet having an arbitrary magnetization direction and having protrusions formed on a surface thereof. An electromagnetic field generation unit (200) sets an alignment direction and a locomotion direction of the microrobot unit to arbitrary directions in the 3D space, generates magnetic fields, and then drives the microrobot unit so that the microrobot unit is rotated by itself or is propelled in the locomotion direction. An imaging unit (300) captures an X-ray image and then tracking a location of the microrobot unit.

2 Claims, 11 Drawing Sheets (51) Int. Cl.
  *A61B 6/12* (2006.01)
  *A61B 19/00* (2006.01)
  *A61N 2/00* (2006.01)

(52) U.S. Cl.
  CPC ........ *A61N 2/002* (2013.01); *A61B 2019/2219* (2013.01); *A61B 2019/2249* (2013.01); *A61B 2019/2253* (2013.01); *A61B 2019/5238* (2013.01)

(56) References Cited

U.S. PATENT DOCUMENTS

| | | | |
|---|---|---|---|
| 7,962,194 B2 * | 6/2011 | Martel et al. | 600/411 |
| 8,694,092 B2 * | 4/2014 | Ferren et al. | 607/2 |
| 2004/0210128 A1 * | 10/2004 | Martel et al. | 600/411 |
| 2008/0278492 A1 * | 11/2008 | Ruijters et al. | 345/426 |
| 2009/0281418 A1 * | 11/2009 | Ruijters et al. | 600/424 |
| 2011/0215888 A1 * | 9/2011 | Abbott et al. | 335/229 |
| 2013/0303888 A1 * | 11/2013 | Deladi et al. | 600/424 |

FOREIGN PATENT DOCUMENTS

| | | |
|---|---|---|
| KR | 10-0999657 B1 | 12/2010 |
| KR | 10-1009053 B1 | 1/2011 |
| WO | WO 2009/145405 A1 | 12/2009 |

* cited by examiner

MICROROBOT SYSTEM FOR INTRAVASCULAR THERAPY AND METHOD OF CONTROLLING THE SAME

TECHNICAL FIELD

The present invention relates, in general, to a microrobot system for intravascular therapy and, more particularly, to a microrobot system for intravascular therapy, which removes thrombus, clots and occlusions that are clogging blood vessels using the fast rotary power of a spherical microrobot having protrusions, thus treating clogged blood vessels.

BACKGROUND ART

Minimally invasive surgery using a microrobot is surgery enabling an incised part to be minimized, the pain of a patient to be reduced, and the recuperation period to be shortened, and a lot of research has been conducted into such minimally invasive surgery. In particular, research into technology for propelling a microrobot or driving the microrobot to administer medical treatment using external magnetic fields has been widely conducted. Most research has been mainly conducted based on a two-dimensional (2D) plane or simple movement performed in a three-dimensional (3D) space.

Korean Patent Registration Nos. KR10-1009053 (entitled "Maintenance and Movement System of Microrobot for Intravascular Therapy") and KR10-0999657 (entitled "Maintenance and Movement System of Microrobot for Intravascular Therapy"), which were recently published, also relate to a microrobot for removing thrombus, clots and occlusions present in blood vessels. However, these technologies are problematic in that the number of coils is large to cause in high power consumption and in that a coil system has the structure of a working space making it difficult to be directly applied to patients.

DISCLOSURE OF INVENTION

Technical Problem

Accordingly, the present invention has been made keeping in mind the above problems occurring in the prior art, and an object of the present invention is to provide a microrobot system for intravascular therapy, in which an electromagnetic field generation unit (a coil system) has the shape of a horizontally arranged cylinder, thus simplifying a working space and performing the same function as that of a conventional coil system that is arranged vertically.

Another object of the present invention is to provide a microrobot system for intravascular therapy, in which a microrobot is formed in a spherical shape, so that drilling and propulsion motions can be driven together without requiring the rotation of coil units, thus easily removing thrombus, clots and occlusions which have accumulated in blood vessels.

A further object of the present invention is to provide a microrobot system for intravascular therapy, in which there is no need to consider the inertia or the like of coil units because the coil units do not rotate, so that the microrobot can be controlled in any direction in a 3D space by controlling only the current without requiring the rotation of the coil units, and in which an X-ray imaging device is also fixed, so that efficient X-ray imaging can be performed even when capturing an internal space.

Solution to Problem

In order to accomplish the above objects, the present invention provides a microrobot system for intravascular therapy, including a spherical microrobot unit including a magnet having an arbitrary magnetization direction and having protrusions formed on a surface thereof; an electromagnetic field generation unit for setting an alignment direction and a locomotion direction of the microrobot unit to arbitrary directions in the 3D space, generating magnetic fields, and then driving the microrobot unit so that the microrobot unit is rotated by itself or is propelled in the locomotion direction; and an imaging unit for capturing an X-ray image and then tracking a location of the microrobot unit.

Further, the present invention provides a method of controlling a microrobot system for intravascular therapy, the microrobot system including a microrobot unit, an electromagnetic field generation unit, and an imaging unit, the method including the electromagnetic field generation unit setting a gradient ($\phi$) of an arbitrary plane on which the microrobot unit is propelled; setting a direction ($\alpha$) of desired propulsion and an intensity (F) of a propulsion force; determining an alignment direction ($\theta$) so as to propel the microrobot unit in a direction of the set; obtaining a gradient ($g_x$) of a magnetic field required to produce a propulsion force using the determined alignment direction ($\theta$); aligning the microrobot unit in the determined alignment direction ($\theta$) on an arbitrary plane having the arbitrary gradient ($\phi$) with respect to an x axis; generating a magnetic field having the constant gradient ($g_x$) and then propelling the microrobot unit; and causing self-rotation (drilling) of the microrobot unit while changing the alignment direction ($\theta$).

Advantageous Effects of Invention

According to the present invention, an electromagnetic field generation unit (a coil system) has the shape of a horizontally arranged cylinder, thus simplifying a working space and performing the same function as that of a conventional coil system that is vertically arranged.

Further, a microrobot is formed in a spherical shape, so that drilling and propulsion can be driven together without requiring the rotation of coil units, thus easily removing thrombus, clots and occlusions accumulated in blood vessels.

BEST MODE FOR CARRYING OUT THE INVENTION

The above and other objects, features and advantages of the present invention will be more clearly understood from the following detailed description taken in conjunction with the accompanying drawings. Further, if in the specification, detailed descriptions of well-known functions or configurations may unnecessarily make the gist of the present invention obscure, the detailed descriptions will be omitted.

Hereinafter, embodiments of the present invention will be described in detail with reference to the attached drawings.

The present invention relates to a microrobot system for intravascular therapy and a method of controlling the microrobot system, and will be described with reference to FIGS. 1 to 7.

Figure 1:
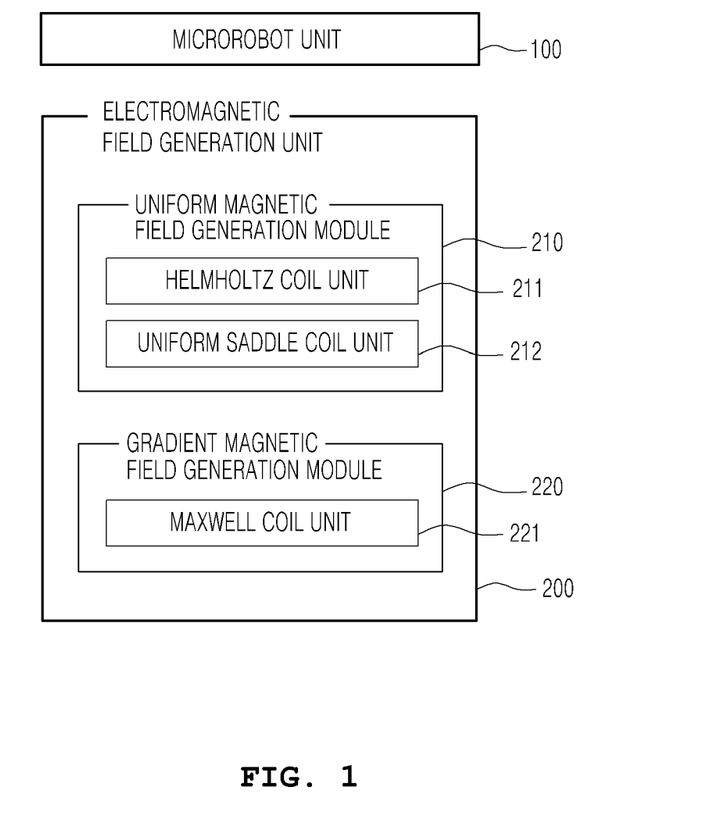
FIG. 1 is a block diagram showing a microrobot system according to an embodiment of the present invention.

FIG. 1 is a block diagram showing a microrobot system according to an embodiment of the present invention, and the microrobot system includes a microrobot unit 100 and an electromagnetic field generation unit 200.

Figure 2A:
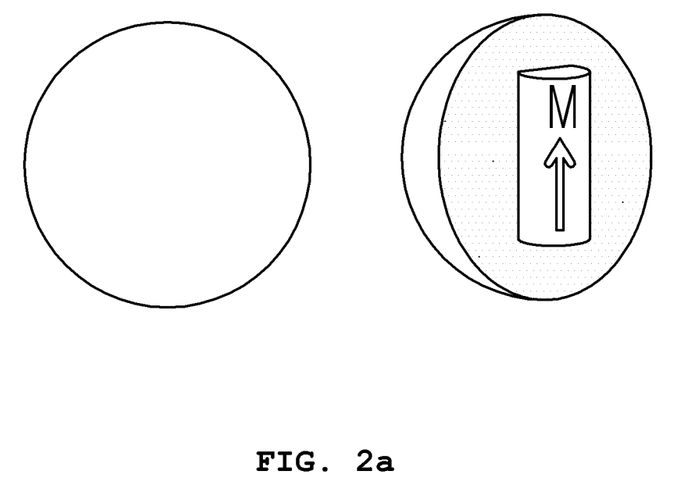
FIG. 2a is a diagram illustrating a spherical microrobot used in the microrobot system according to an embodiment of the present invention and FIG. 2b is a diagram illustrating a spherical microrobot for intravascular therapy used in the microrobot system according to an embodiment of the present invention.

The microrobot unit 100 includes a spherical microrobot including a magnet having an arbitrary magnetization direction. FIG. 2a is a diagram showing a spherical microrobot used in the microrobot system according to an embodiment of the present invention, wherein the microrobot is a spherical microrobot having a magnet. Since the microrobot has a spherical shape, how the magnetization direction is set and included are not important. The magnetization direction of the magnet included in the microrobot is used in a method of aligning the microrobot unit 100, wherein magnetic fields causing the magnetization direction and the aligned direction to be identical to each other are formed, so that the microrobot unit 100 is aligned.

The electromagnetic field generation unit 200 sets the locomotion direction of the microrobot unit 100 to an arbitrary direction in a 3D space, generates magnetic fields, and then drives the microrobot 100 so that the microrobot 100 moves in the arbitrary direction.

Figure 3A:
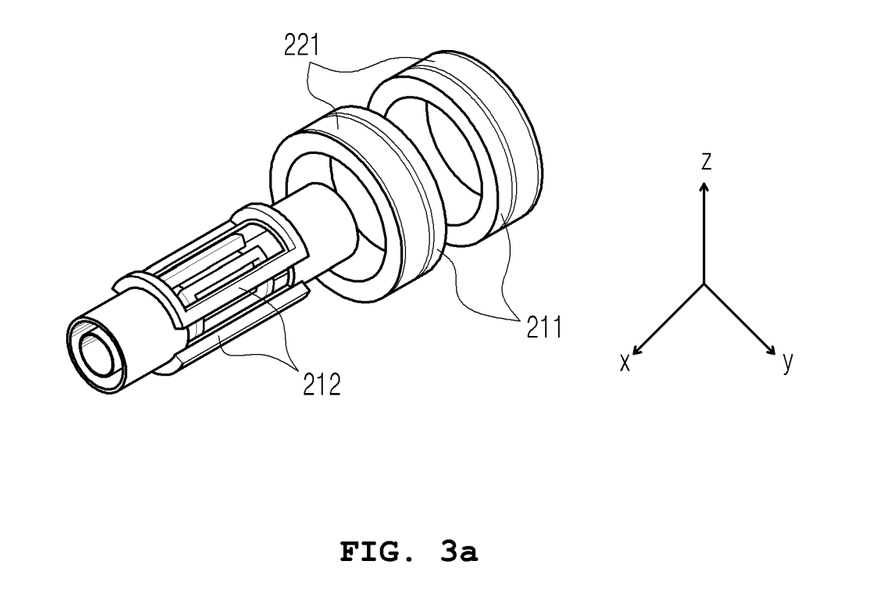
FIG. 3a is an exploded view of an electromagnetic field generation unit used in the microrobot system according to an embodiment of the present invention.
Figure 3B:
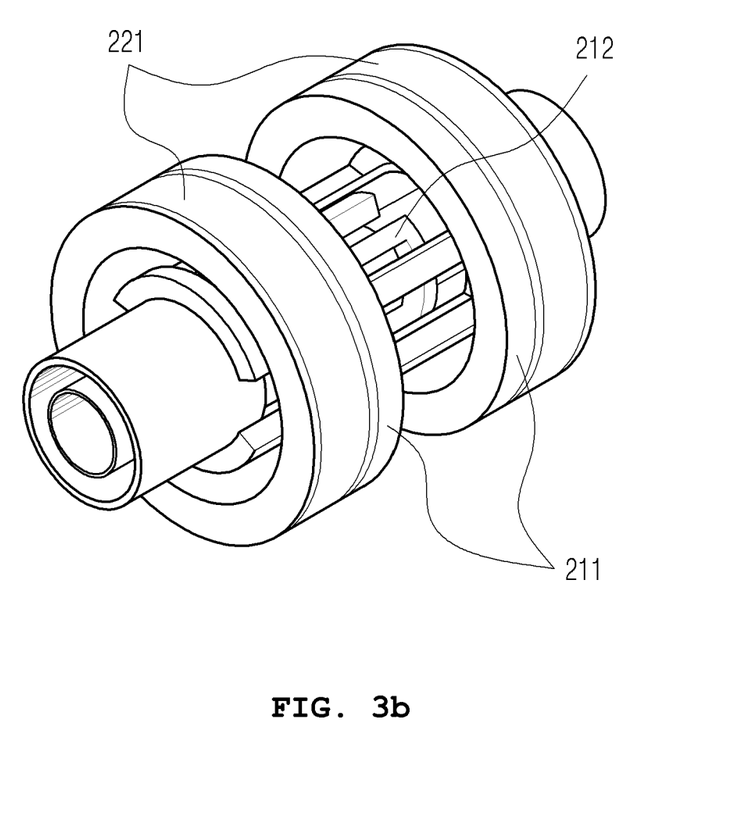
FIG. 3b is an assembled view showing the electromagnetic field generation unit used in the microrobot system according to an embodiment of the present invention.

Referring to FIG. 3a, the electromagnetic field generation unit 200 includes a pair of fixed Helmholtz coil units 211, a pair of fixed Maxwell coil units 221, and two pairs of fixed uniform saddle coil units 212.

The electromagnetic field generation unit 200 includes a uniform magnetic field generation module 210 for aligning the microrobot unit 100 in the arbitrary direction in the 3D space, and generating uniform magnetic fields so that the microrobot unit 100 rotates by itself while changing the alignment direction thereof, and a gradient magnetic field generation module 220 for generating magnetic fields having a constant gradient so that a propulsion force is produced to allow the microrobot to move in the alignment direction.

The uniform magnetic field generation module 210 forms uniform magnetic fields in arbitrary directions in a 3D space of the x, y, and z axes by using the one pair of Helmholtz coil units 211 which are oppositely arranged along an arbitrary axis in the 3D space, and the two pairs of uniform saddle coil units 212 which are located on a plane perpendicular to the arbitrary axis and are fixedly installed to be orthogonal to each other, that is, by using a total of three pairs of fixed coils. Referring to FIG. 3a, when, on the basis of the x axis, the one pair of Helmholtz coil units 211 are installed to be oppositely arranged along the x axis, a magnetic field can be formed in the direction of the x axis. When the two pairs of fixed uniform saddle coil units 212 are located on a y-z plane perpendicular to the x axis, and are installed so that the two pairs of fixed uniform saddle coil units 212 are oppositely arranged to be orthogonal to each other, uniform magnetic fields can be respectively formed in the directions of the y and z axes perpendicular to the x axis. By controlling the magnitudes of currents flowing through the respective axes, magnetic fields can be formed in any of the directions in the 3D space.

The gradient magnetic field generation module 220 includes the one pair of Maxwell coil units 221 that are oppositely arranged along the same axis as the axis along which the Helmholtz coils are arranged. For conventional coil units used to generate a propulsion force, rotatable gradient saddle coils may also be used. However, the present system is intended to implement a coil system for the drilling motion of the spherical microrobot, and is characterized in that since the microrobot actually has a spherical shape, there is no need to use rotatable coil units when causing the alignment direction to be identical to the propulsion direction, and it is possible to produce a propulsion force using only one pair of fixed Maxwell coils. In the present invention, rotatable gradient saddle coils are not used, so that manufacturing costs are reduced, and a working space allowing a patient to more easily get in can be ensured.

Since the rotatable coil units are not used in the present invention, the inertia of the coils does not need to be taken into consideration, and X-ray images can also be efficiently captured.

The microrobot is propelled in a locomotion direction using the electromagnetic field generation unit 200, and implements self-rotation, that is, a drilling motion. A method of controlling this operation will be described with reference to FIG. 4.

Figure 4A:
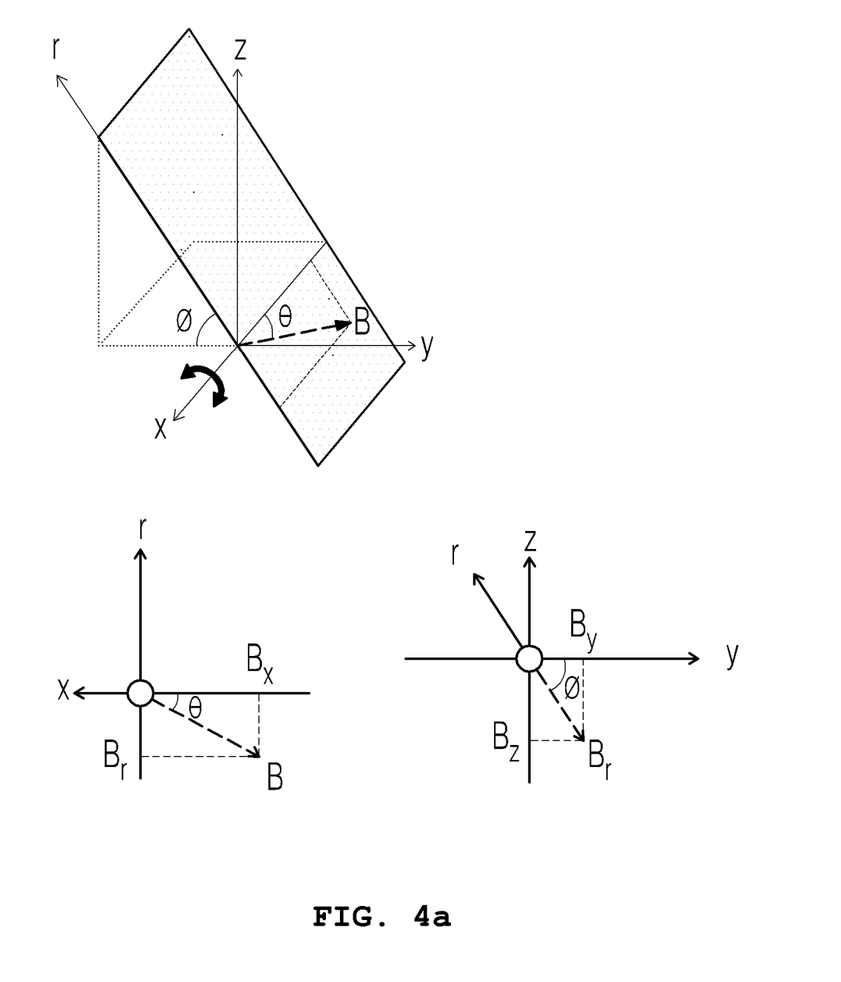
FIG. 4a is a diagram showing the magnitudes and directions of magnetic fields required to set the alignment direction of a microrobot unit according to an embodiment of the present invention.

FIG. 4a is a diagram showing the magnitudes and directions of magnetic fields required to set the alignment direction of the microrobot unit 100 according to an embodiment of the present invention. The microrobot unit 100 used in the present system has a fully spherical body, so that front and rear parts thereof are not discriminated between, and thus the microrobot unit 100 is not greatly influenced by the magnetization direction. In this case, the microrobot unit 100 is aligned in a predetermined direction using a method which makes the alignment direction identical to the magnetization direction. When the angle of alignment is assumed to be θ, magnetic fields required at that time are given by the following Equation (1):

$$B = \begin{bmatrix} B_x \\ B_y \\ B_z \end{bmatrix} = \begin{bmatrix} |B|\sin\theta \\ |B|\cos\theta\sin\phi \\ -|B|\cos\theta\cos\phi \end{bmatrix} \quad (1)$$

where θ denotes the alignment direction, and ϕ denotes the angle formed between a plane, rotated clockwise around the x axis, and the X axis. That is, the magnetic field 'B' in Equation (1) denotes 'magnitude and direction of each magnetic field' required to align the microrobot unit 100 in the direction of θ on an arbitrary plane forming an angle of ϕ with respect to the x axis. Here, θ and φ must be set as different values depending on the actual target, |B| denotes the magnitude of the magnetic field, and the symbol (+)/(−) denotes the direction of the magnetic field.

Meanwhile, θ is related to the propulsion direction. When the propulsion direction is assumed to be α, a correlation between α and θ is required. The reason for this is that the propulsion direction of the microrobot may be changed in the present system depending on how the microrobot is aligned.

In this case, θ is given by the following Equation (2):

$$\theta = \tan^{-1}\left(\frac{2(F\sin\alpha + mg\sin\phi)}{F\cos\alpha}\right) \quad (2)$$

where F denotes the intensity of the propulsion force, α denotes the direction of the propulsion force, and φ denotes an angle formed between the plane, rotated clockwise around the x axis, and the x axis, as described above.

In practice, in order to drive the present system, a desired propulsion direction α and the intensity F of the propulsion force are determined. Since φ is the angle formed between the plane, rotated clockwise around the x axis, and the x axis, F, α and φ are values basically set according to the target. Once F, α, and φ have been determined, the angle of the alignment direction, that is, θ, is determined.

Once θ has been determined, the uniform magnetic fields in Equation (1) are generated by combining the one pair of Helmholtz coil units 211 and the two pairs of uniform saddle coils 212.

Figure 4B:
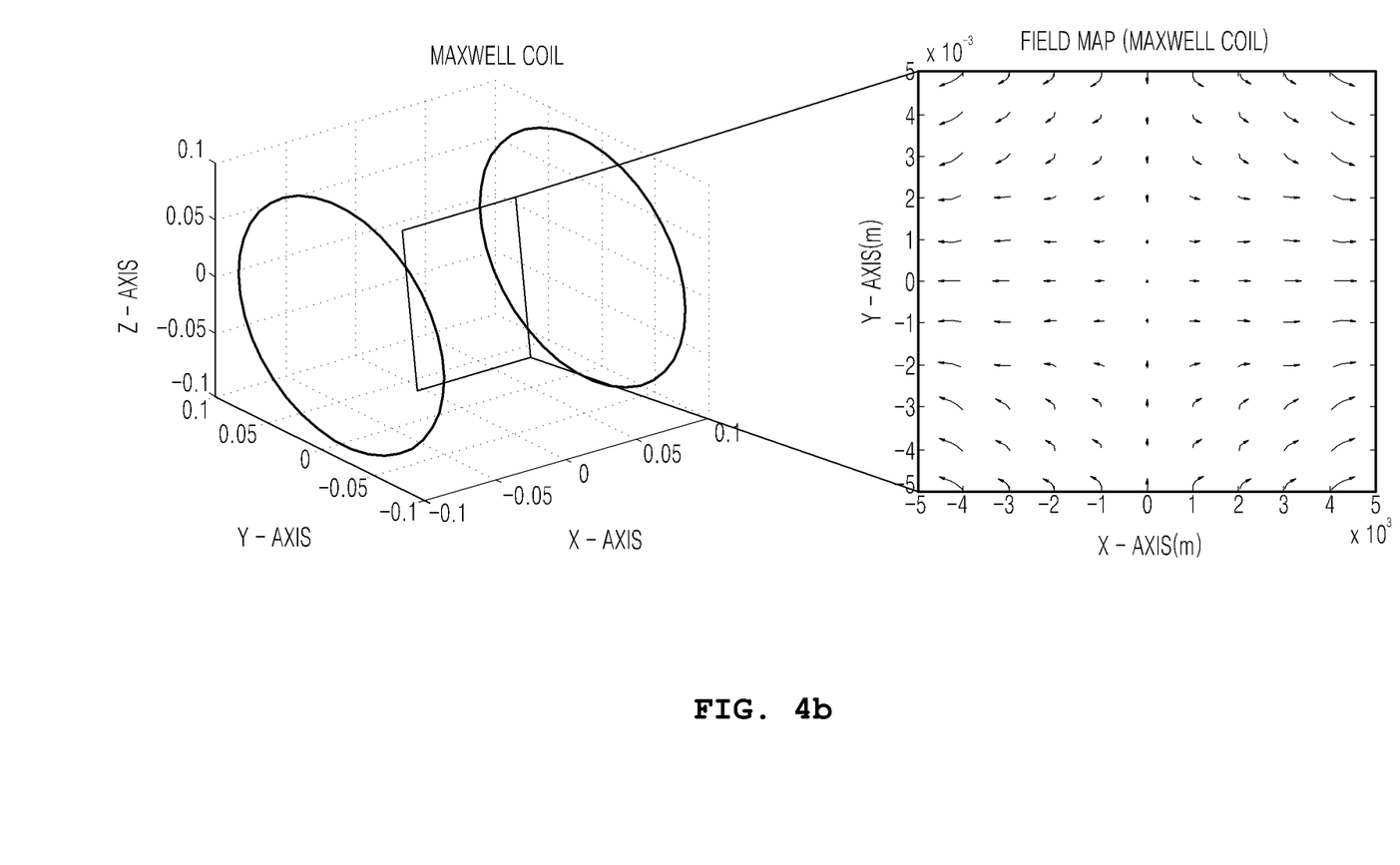
FIG. 4b is a diagram showing a map of magnetic fields generated by Maxwell coils according to an embodiment of the present invention.

FIG. 4b is a diagram showing a map of magnetic fields generated by the Maxwell coils according to an embodiment of the present invention. The Maxwell coils generate a magnetic field that has a constant gradient in an axial direction. However, the Maxwell coils have a property in which magnetic fields having a half magnitude and having a constant gradient in the opposite direction are generated in directions perpendicular to the main axial direction. Due to such a property, the propulsion force can be produced in a specific direction. The magnetic fields generated at this time are given by the following Equation (3):

$$B = \begin{bmatrix} B_x \\ B_y \\ B_z \end{bmatrix} = \begin{bmatrix} g_x x \\ -0.5g_x y \\ -0.5g_x z \end{bmatrix} \quad (3)$$

In this case, φ can be used instead of y-z, wherein if an axis rotated clockwise around the x axis at an angle of φ is defined as an r axis, the magnetic fields generated at this time are given by the following Equation (4):

$$B = \begin{bmatrix} B_x \\ B_r \end{bmatrix} = \begin{bmatrix} g_x x \\ -0.5g_x r \end{bmatrix} \quad (4)$$

where $g_x$ denotes the gradient of the magnetic field generated in the direction of the x axis using the Maxwell coils on the x axis. $g_x$ is required to produce the propulsion force of the microrobot unit 100, and the gradient $g_x$ of the magnetic field that must be generated by the Maxwell coil units 221 is represented by the following Equation (5):

$$g_x = \frac{F\cos\alpha}{MV\cos\theta} \quad (5)$$

where F is defined as the intensity of the propulsion force, α is defined as the direction of the propulsion force, θ is defined as the alignment direction, M is defined as the intensity of magnetization of the magnet included in the microrobot unit 100, and V is defined as the volume of the magnet. Using these parameters, the magnetic field formed by the Maxwell coil units 221 is obtained.

Figure 4C:
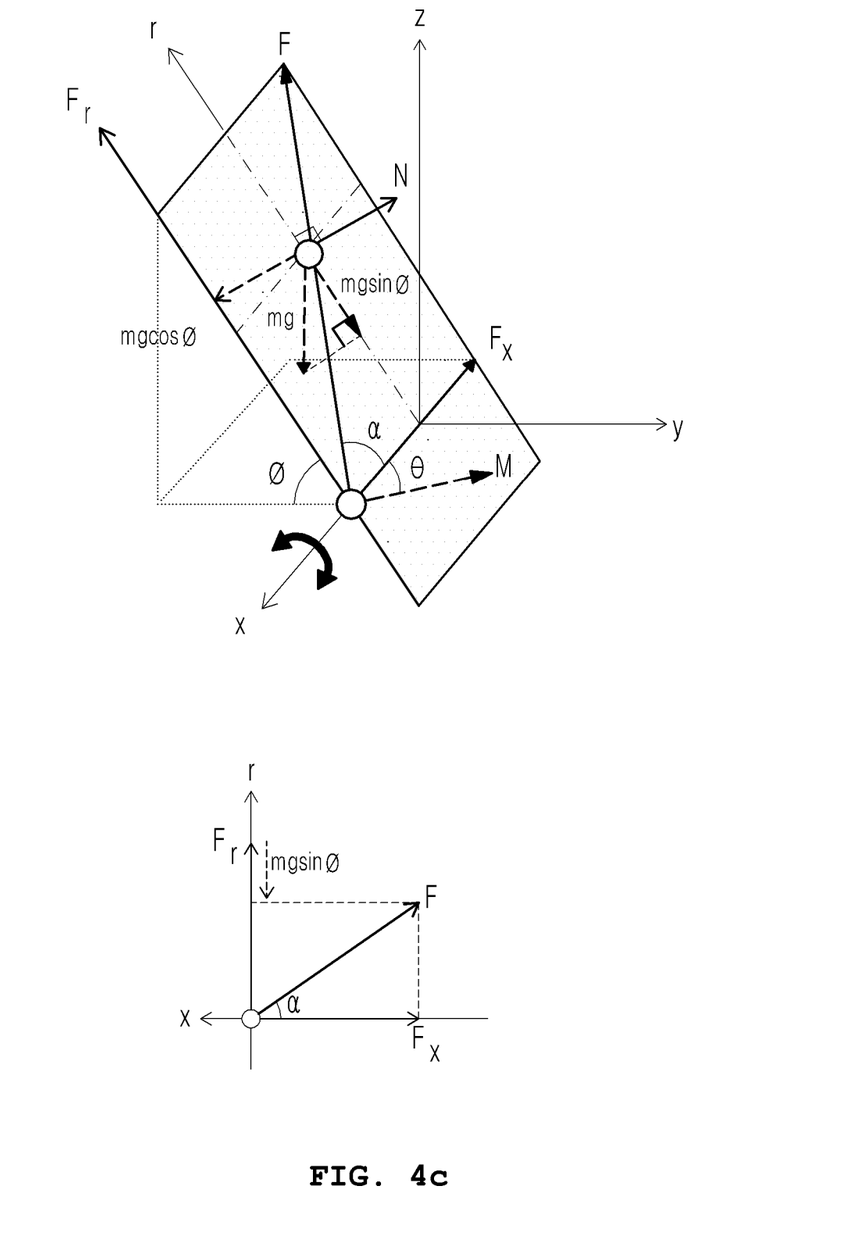
FIG. 4c is a diagram showing the intensity and direction of a force applied to a microrobot propelled in a specific direction on an arbitrary plane according to an embodiment of the present invention.

FIG. 4c is a diagram showing the intensity and direction of a force applied to the microrobot being propelled in a specific direction on an arbitrary plane according to an embodiment of the present invention. In FIG. 4c, the microrobot is aligned using one pair of Helmholtz coil units 211 and two pairs of uniform saddle coil units 212, and thereafter a magnetic field having a gradient of $g_x$ is formed using the Maxwell coils, so that the microrobot unit 100 is propelled in the direction of α.

Figure 4D:
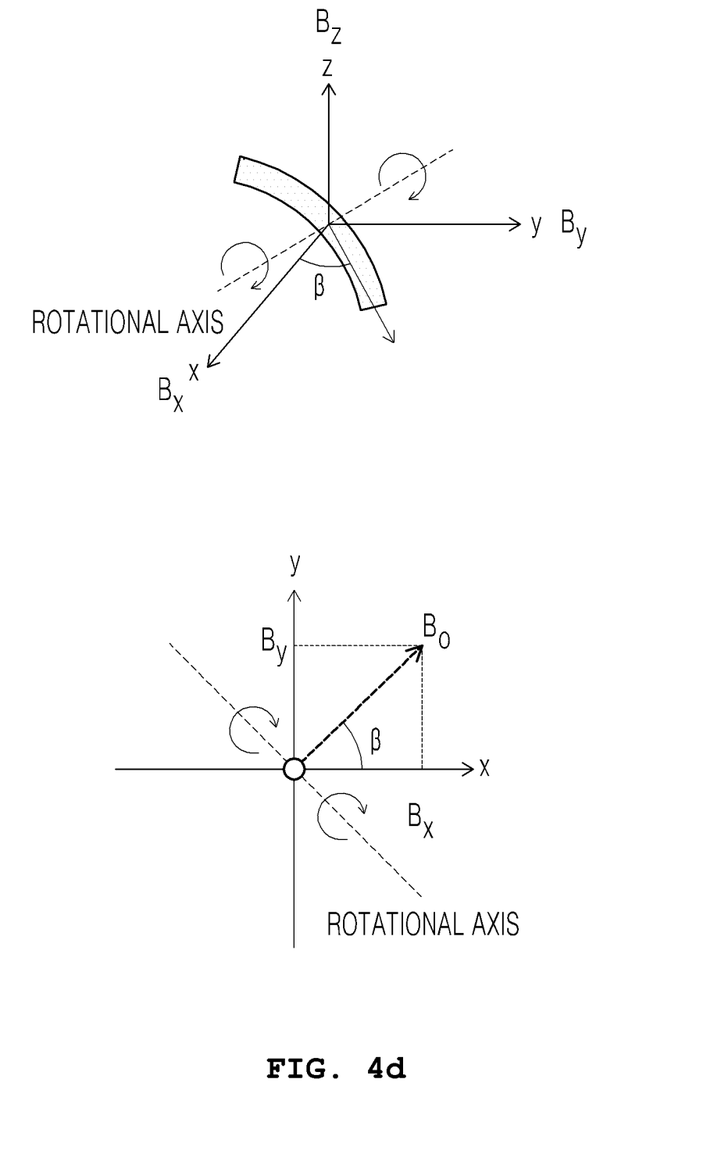
FIG. 4d is a diagram showing a rotational axis and a rotational direction required to drive a rotational motion according to an embodiment of the present invention.

FIG. 4d is a diagram showing a rotational axis and a rotational direction required to drive a rotational motion according to an embodiment of the present invention. In the drawing, the microrobot unit 100 can be rotated by itself while changing θ of Equation (2) using the Helmholtz coil units and the uniform saddle coil units. As the rotational speed becomes higher, the drilling motion of the robot unit can be performed.

Figure 5:
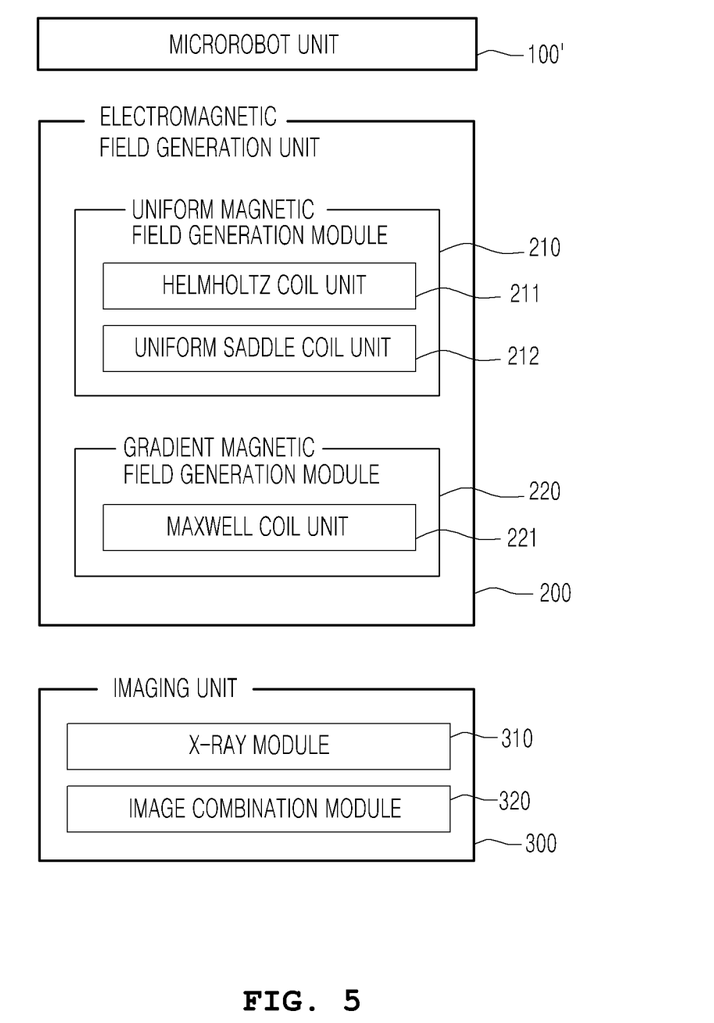
FIG. 5 is a block diagram showing the configuration of a microrobot system for intravascular therapy according to an embodiment of the present invention.
Figure 6:
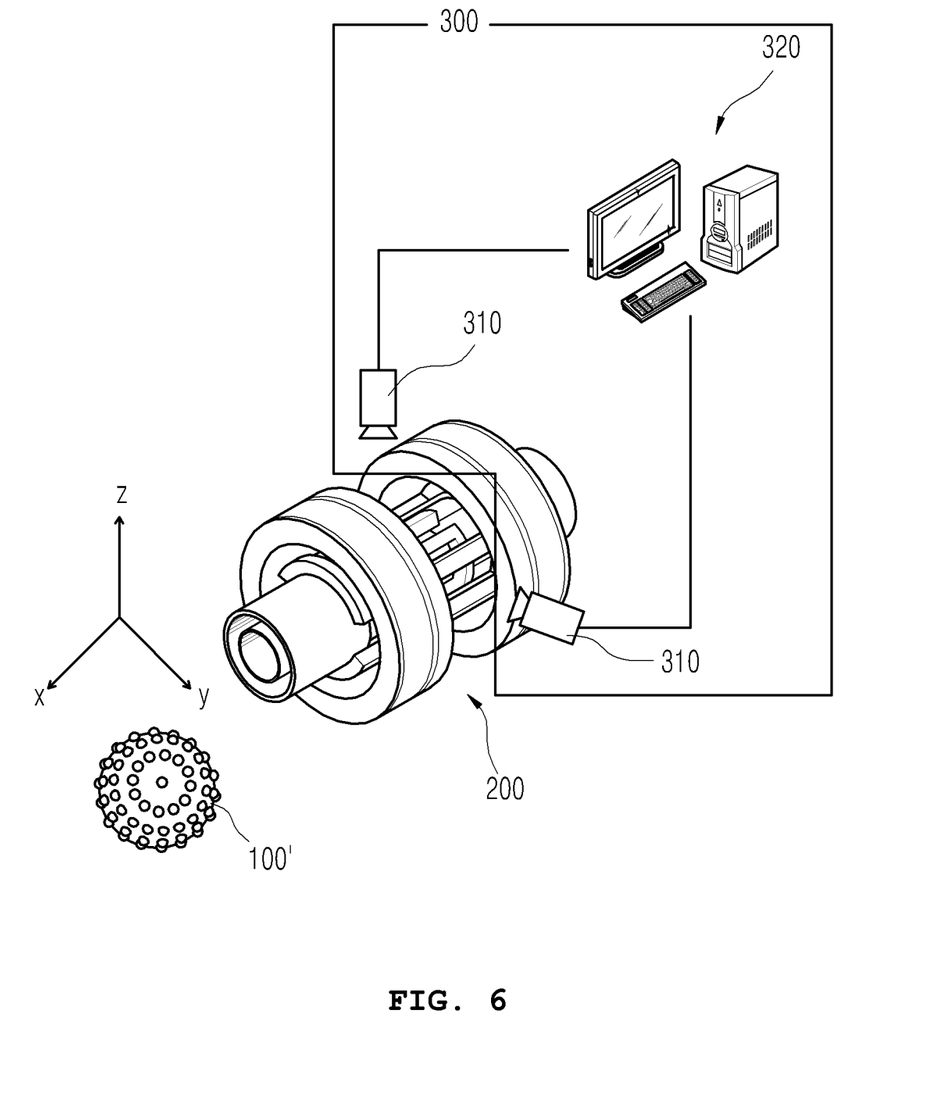
FIG. 6 is a configuration diagram showing the microrobot system for intravascular therapy according to an embodiment of the present invention.

FIG. 5 is a block diagram showing the configuration of a microrobot system for intravascular therapy according to an embodiment of the present invention, and FIG. 6 is a configuration diagram showing the microrobot system for intravascular therapy according to an embodiment of the present invention. The microrobot system includes a microrobot unit 100' for intravascular therapy, an electromagnetic field generation unit 200, and an imaging unit 300.

The microrobot unit 100' includes a magnet having an arbitrary magnetization direction and has protrusions formed on the spherical surface thereof. Referring back to FIG. 2b, a plurality of convex protrusions are formed and distributed on the outer circumference of the spherical microrobot. The protrusions on the outer circumference can be manufactured to suit the size of a blood vessel. Methods of manufacturing the robot may be implemented using a method of forming protrusions using a material harmless to the human body, such as diamond powder or stainless steel, around a permanent magnet, or a method of manufacturing a spherical robot having protrusions using a material, such as diamond powder or stainless steel, and inserting a permanent magnet into the spherical robot. The height or width of the protrusions can be determined using the internal diameter or the like of a targeted blood vessel.

Figure 2B:
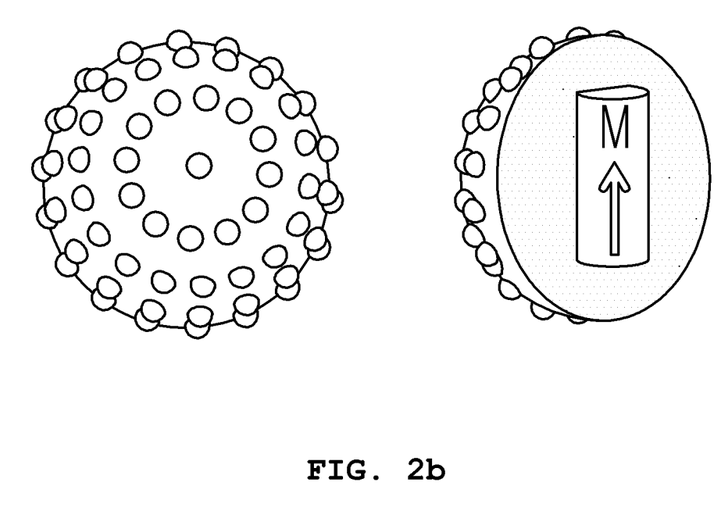

Since the microrobot used in the present system has a spherical shape, the propulsive driving of the microrobot can be performed while the drilling motion of the microrobot can be performed in a desired direction. Since thrombus, clots and occlusions accumulated in blood vessels can be removed using the protrusions formed on the microrobot unit 100', the microrobot can be used to treat blood vessels.

The electromagnetic field generation unit 200 sets the locomotion direction of the microrobot unit 100' to an arbitrary direction in a 3D space, and generates magnetic fields, so that the microrobot unit 100' is driven to move in the arbitrary direction.

Referring to FIG. 3a, the electromagnetic field generation unit 200 includes a pair of fixed Helmholtz coil units 211, a pair of fixed Maxwell coil units 221, and two pairs of fixed uniform saddle coil units 212.

The electromagnetic field generation unit 200 includes a uniform magnetic field generation module 210 for aligning the microrobot unit 100' in an arbitrary direction in the 3D space, and generating uniform magnetic fields so that the microrobot unit 100' is rotated by itself (self-rotation) while changing the alignment direction thereof, and a gradient magnetic field generation module 220 for generating magnetic fields having constant acceleration so that a propulsion force is produced to allow the microrobot to move in the alignment direction.

The uniform magnetic field generation module 210 forms uniform magnetic fields in arbitrary directions in the 3D space defined by x, y and z axes by using the one pair of Helmholtz coil units 211 oppositely arranged along an arbitrary axis in the 3D space and the two pairs of fixed uniform saddle coil units 212 located on a plane perpendicular to the arbitrary axis and fixedly installed to be orthogonal to each other, that is, by using a total of three pairs of fixed coils. Referring to FIG. 3a, when, on the basis of the x axis, the one pair of Helmholtz coil units 211 are installed to be oppositely arranged along the x axis, a magnetic field can be formed in the direction of the x axis. When the two pairs of fixed uniform saddle coil units 212 are located on a y-z plane perpendicular to the x axis, and are installed so that the two pairs of fixed uniform saddle coil units 212 are oppositely arranged to be orthogonal to each other, uniform magnetic fields can be respectively formed in the directions of the y and z axes perpendicular to the x axis. By controlling the magnitudes of currents flowing through the respective axes, magnetic fields can be formed in any of the directions in the 3D space.

The gradient magnetic field generation module 220 includes the one pair of Maxwell coil units 221 that are oppositely arranged along the same axis as the axis along which the Helmholtz coils are arranged. For conventional coil units used to generate a propulsion force, rotatable gradient saddle coils may also be used. However, the present system is intended to implement a coil system for the drilling motion of the spherical microrobot, and is characterized in that since the microrobot actually has a spherical shape, there is no need to cause the alignment direction to be identical to the propulsion direction, so that rotatable coil units are not required, and thus it is possible to produce a propulsion force using only one pair of fixed Maxwell coils.

Since the rotatable coil units are not used in the present invention, the inertia of the coils does not need to be taken into consideration, and X-ray images can also be efficiently captured.

The imaging unit 300 captures the location of the microrobot unit 100' in real time using an X-ray imaging device mounted on the electromagnetic field generation unit 200. In this case, when there is a Computed Tomography (CT) or Magnetic Resonance (MR) image captured before a surgical operation, such an image can be combined with X-ray images captured in real time. Such combined images can be used to recognize and track in real time the location of the microrobot unit 100'. The imaging unit 300 includes X-ray modules 310 for capturing the location of the microrobot unit 100' while the microrobot is being driven, and an image combination module 320 for combining a previously captured image with the images captured by the X-ray modules 310, and then tracking and displaying the location of the microrobot unit 100'.

Figure 7:
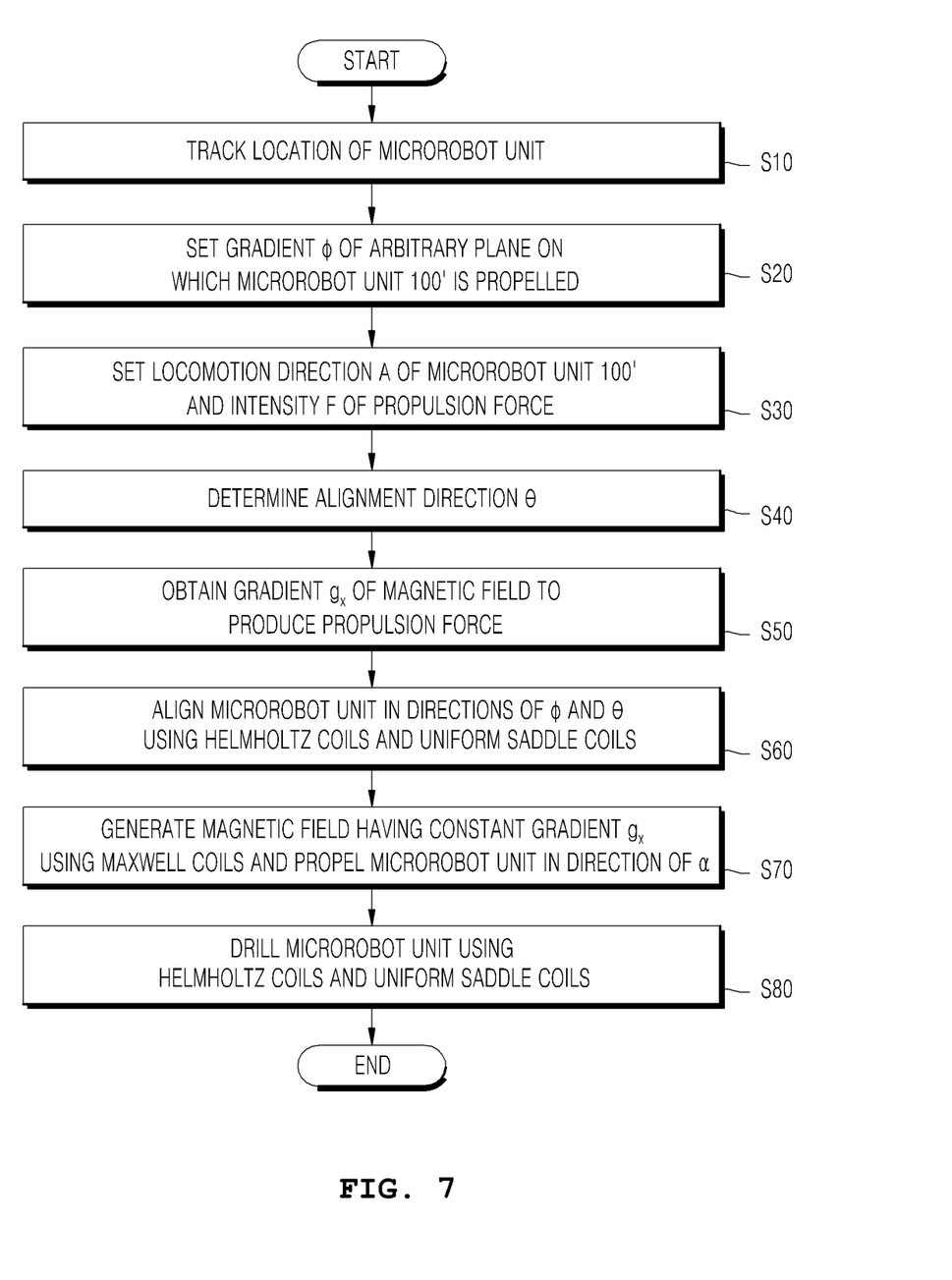
FIG. 7 is a flowchart showing a method of controlling the microrobot system for intravascular therapy according to an embodiment of the present invention.

FIG. 7 is a flowchart showing a method of controlling the microrobot system for intravascular therapy according to an embodiment of the present invention. The method will be described below with reference to this drawing.

First, the location of the microrobot unit 100 is tracked in real time using the X-ray modules 310 fixedly installed on the electromagnetic field generation unit 200 at step S10. When the imaging unit 300 captures the location of the microrobot unit 100' as images while the microrobot unit 100' is being driven at step S11, the imaging unit 300 combines a previously captured image with the images captured at step Sib at step S12. The imaging unit 300 tracks the location of the microrobot unit 100' while tracking and displaying the location of the microrobot unit 100' using the images combined at step S12. This procedure is identical to a typical method of tracking the location of a microrobot, and thus a detailed description thereof will be omitted.

Thereafter, in order to set the plane on which a propulsion function is desired, the gradient $\phi$ of an arbitrary plane on which the microrobot unit 100' is desired to be propelled is set at step S20, and the locomotion direction $\alpha$ of the microrobot unit 100' and the intensity F of a propulsion force are set at step S30. Thereafter, the alignment direction $\theta$ of the microrobot unit 100' is determined in consideration of the locomotion direction and the propulsion force at step S40. $\theta$ is determined by the above Equation (2), where $\phi$ denotes an angle formed between the plane, rotated clockwise around the x axis, and the x axis, and F, $\alpha$, and $\phi$ may be set in the initiation stage of the system according to the target.

After step S40, the gradient $g_x$ of the magnetic fields is obtained to produce the propulsion force using the Maxwell coil units 221 at step S50. $g_x$ is determined by the above-described Equation (5).

The procedure from step S20 to step S50 is the procedure of setting values for generating electromagnetic fields. Once these values have been set, uniform magnetic fields are formed in the directions of $\phi$ and $\theta$ using the one pair of Helmholtz coil units 211 and the two pairs of uniform saddle coil units 212, so that the microrobot unit 100' is aligned at step S60. A method of forming the uniform magnetic fields in the directions of $\phi$ and $\theta$ may be implemented as a method of controlling the currents in the directions of $\phi$ and $\theta$ by adjusting the magnitudes of the currents, and of causing the directions of the currents flowing through the coil units to be identical, thus forming the uniform magnetic fields.

The magnetization direction of the magnet inside the microrobot unit 100' is not important. By using a method of aligning the magnetization direction with the alignment direction, the microrobot unit 100' is aligned. When the microrobot having an actually fully spherical body is used, there is no great problem even if the alignment direction and the locomotion direction are different from each other.

After step S60, magnetic fields having a constant gradient $g_x$ are generated using the Maxwell coil units, so that the microrobot unit 100' is propelled in the direction of $\alpha$ at step S70. The Maxwell coil units 221 generate the magnetic fields having a constant gradient, unlike the Helmholtz coil units 211. At this time, the gradient $g_x$ is determined by the above Equation (5), is influenced by the locomotion direction $\alpha$ and the alignment direction $\theta$, and has a larger gradient value as the propulsion force F is larger. That is, when the magnitude of the current is larger, the propulsion force is larger, and this is represented by a larger gradient value.

At step S70, only a function of simply propelling the microrobot unit 100' forwards is performed, and a rotational motion is not performed. In order to implement a rotational motion, that is, a so-called drilling motion while the microrobot is actually rotated by itself at higher speed, rotary power required for rotation must be produced. The rotary power can be produced using the Helmholtz coils and the uniform saddle coils. When the alignment direction $\theta$ formed by one pair of Helmholtz coils and two pairs of uniform saddle coils is promptly changed, a drilling motion making self-rotation is consequently performed while the alignment direction is continuously changed at step S80. In particular, the present system uses one pair of Helmholtz coils and two pairs of uniform saddle coils, that is, a total of three pairs of fixed coils, instead of rotatable uniform saddle coils, so that there is no need to rotate the coils by as many times as the microrobot unit 100 performs self-rotation, thus obtaining the advantage of enabling a drilling motion requiring fast rotation.

As described above, although the preferred embodiments of the present invention for exemplifying the technical spirit thereof have been disclosed for illustrative purposes, those skilled in the art will appreciate that the present invention is not limited by the construction and operation illustrated and described in the above embodiments, and various modifications and changes are possible, without departing from the spirit and scope of the invention. Therefore, it should be understood that all suitable modifications and changes and equivalents thereof belong to the scope of the present invention.

The invention claimed is:

1. A microrobot system for intravascular therapy, comprising:
   a microrobot unit having a spherical shape and having protrusions formed over the entire surface thereof, the microrobot unit including a magnet having an arbitrary magnetization direction;
   an electromagnetic field generation unit setting an alignment direction and a locomotion direction of the microrobot unit to arbitrary directions in the 3D space, generating magnetic fields, and driving the microrobot unit so that the microrobot unit is rotated by itself or is propelled in the locomotion direction, the electromagnetic field generation unit including
      a pair of Helmholtz coil units oppositely arranged along an arbitrary axis in the 3D space,
      a pair of Maxwell coil units oppositely arranged along an axis identical to the arbitrary axis, and
      two pairs of fixed uniform saddle coil units located inside of the pair of Helmholtz coil units and the pair of Maxwell coil units and fixedly installed on a plane perpendicular to the arbitrary axis and not rotating about the arbitrary axis, the two pairs of fixed uniform saddle coil units being disposed to be orthogonal to each other; and
   an imaging unit capturing X-ray images and tracking a location of the microrobot unit, the imaging unit including
      at least one X-ray module capturing a first X-ray image of the microrobot unit in real time to locate the microrobot unit while the microrobot unit is being driven, and
      an image combination module combining the first X-ray image captured in real time with a second image captured before the surgical operation, thereby tracking and displaying the location of the microrobot unit.

2. A method of controlling a microrobot system for intravascular therapy, the microrobot system including a microrobot unit which has a spherical shape, has protrusions formed over the entire surface thereof, and includes a magnet having an arbitrary magnetization direction, an electromagnetic field generation unit which includes a pair of Helmholtz coil units oppositely arranged along an arbitrary axis in the 3D space, a pair of Maxwell coil units oppositely arranged along an axis identical to the arbitrary axis, and two pairs of fixed uniform saddle coil units located inside of the pair of Helmholtz coil units and the pair of Maxwell coil units and fixedly installed on a plane perpendicular to the arbitrary axis other and not rotating about the arbitrary axis, the two pairs of fixed uniform saddle coil units being disposed to be orthogonal to each, and an imaging unit, the method comprising:
   (a) capturing, by the imaging unit, a first X-ray image of the microrobot unit in real time to locate the microrobot unit while the microrobot unit is being driven;
   (b) combining, by the imaging unit, the first X-ray image captured in real time with a second image captured before the surgical operation;
   (c) tracking and displaying, by the imaging unit, a location of the microrobot unit using the image combined in step (b);
   (d) setting, by the electromagnetic field generation unit, a gradient ($\phi$) of an arbitrary plane on which the microrobot unit is propelled;
   (e) setting, by the electromagnetic field generation unit, a direction ($\alpha$) in which the microrobot unit is propelled and an intensity (F) of a propulsion force;
   (f) determining, by the electromagnetic field generation unit, an alignment direction ($\theta$) so as to propel the microrobot unit to the direction set in steps (d) and (e);
   (g) obtaining, by the electromagnetic field generation unit, a gradient (gx) of a magnetic field required to produce a propulsion force using the alignment direction ($\theta$) determined in step (f);
   (h) aligning, by a uniform magnetic field generation module of the electromagnetic field generation unit, the microrobot unit in the alignment direction (8) determined in step (f) on an arbitrary plane having the arbitrary gradient ($\phi$) with respect to an x axis;
   (i) generating, by a gradient magnetic field generation module of the electromagnetic field generation unit, a magnetic field having the constant gradient (gx) obtained in step (g) and then propelling the microrobot unit; and
   (j) causing, by the uniform magnetic field generation module, self-rotation (drilling) of the microrobot unit while changing the alignment direction ($\theta$).

* * * * *